United States Patent [19]

Caupin et al.

[11] Patent Number: 5,539,034
[45] Date of Patent: Jul. 23, 1996

[54] COMPOSITION CONTAINING A POLYMER RESIN AND UNDECYLENIC ACID OR DERIVATIVES THEREOF

[75] Inventors: Henri J. Caupin, Versailles; Roland Leroux, Chaville, both of France

[73] Assignee: ELF Atochem S.A., Puteaux, France

[21] Appl. No.: 461,760

[22] Filed: Jun. 5, 1995

Related U.S. Application Data

[63] Continuation of Ser. No. 148,559, Nov. 8, 1993, abandoned.

[30] Foreign Application Priority Data

Nov. 6, 1992 [FR] France ................................ 92 13369

[51] Int. Cl.$^6$ ................................................ C08K 5/10
[52] U.S. Cl. .................... 524/315; 524/301; 524/322; 523/351; 424/65; 424/404; 514/858
[58] Field of Search ............................. 524/322, 301, 524/315; 523/351; 424/65, 404; 514/858

[56] References Cited

U.S. PATENT DOCUMENTS 4,734,278  3/1988  Pougalan et al. ................ 424/76.3

FOREIGN PATENT DOCUMENTS 2173208  10/1986  United Kingdom .

OTHER PUBLICATIONS

CA, vol. 107, No. 16, 19 Oct. 1987, 140915e.
CA, vol. 107, No. 16, 19 Oct. 1987, 140884u.
Data Base Chemical Abstracts (Host STN), vol. 107, No. 16, 19 Oct. 1987, abrege no. 140915e, Columbus, Ohio, US; & JP-A-62 101 201 (Kichiyoshi Shiko) 11-05-1987.
Data Base Chemical Abstracts (Host STN), vol. 107, No. 16, 19 Oct. 1987, abrege No. 140884u, Columbus, Ohio, US; & JP-A-62 038 101 (K. Hirano) 19-02-1987.

*Primary Examiner*—Paul R. Michl
*Assistant Examiner*—John J. Guarriello
*Attorney, Agent, or Firm*—Burns, Doane, Swecker & Mathis

[57] ABSTRACT

A stable composition having a deodorizing action includes a sequenced polyetheresteramide polymer and an undecylenic acid or a lipid-soluble or water-soluble derivative thereof. Suitable derivatives include the $C_1$ to $C_6$ alkyl esters of undecylenic acid.

14 Claims, No Drawings

COMPOSITION CONTAINING A POLYMER RESIN AND UNDECYLENIC ACID OR DERIVATIVES THEREOF

This application is a continuation of application Ser. No. 08/148,559, filed Nov. 8, 1993, now abandoned.

BACKGROUND OF THE INVENTION

The present invention relates to a novel product comprising a polymer resin carrier incorporating undecylenic acid or derivatives thereof and to a process for preparing said resin.

Undecylenic acid or derivatives thereof such as esters and metal salts, particularly alkaline or alkaline-earth metal salts, is known on account of its numerous properties.

Several documents describe the pediculicidal (lice destroying) action of undecylenic acid or its derivazives, notably the lower alkyl ester derivatives.

Several documents describe the fungicidal action of undecylenic acid.

Then again, several documents describe its deodorant action, in the sense that this $C_{11}$ acid is able to remove unpleasant odors from air.

Now, regarding the said deodorant action for example, it would be advantageous to provide a support matrix or carrier for the said acid or its derivatives, in order to obtain easy-to-use deodorant sticks.

FR-A-2 579 983 discloses a polymer resin based on polyetheresteramide (PEEA) in its use as a support for perfumes, the said resin providing for their release. This patent concerns the release of a perfume, in other words the provision of an odorising action through a diffusion mechanism, having a masking effect. There is no mention of a deodorant action and no mention of destroying unpleasant smells.

SUMMARY OF THE INVENTION

The present invention consequently provides a stable composition comprising, by weight, based on the weight of said composition:

(a) 90 to 5% by weight of a sequenced polyetheresteramide polymer of formula:

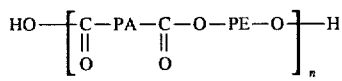

in which PA represents the polyamide segment and PE represents the polyether segment, n is an integer representing the distribution of the recurrent units; and (b) 10 to 95% by weight of undecylenic acid, or derivatives thereof, the weight of said derivatives being calculated based on the corresponding weight of undecylenic acid.

This PEEA polymer is obtained by any suitable process; in particular, the polyether-ester-amide resin is obtained by the reaction, in the molten state, between a dicarboxylic polyamide having terminal carboxylic functions of an average molecular weight comprised between 300 and 15000 and a linear or branched aliphatic polyoxyalkylene glycol having terminal hydroxyl functions and an average molecular weight comprised between 200 and 6000, under high vacuum at temperatures comprised between 100° and 400° C. in the presence of a catalyst which is, for example, a tetraalkyl-orthotitanate of general formula $Ti(OR)_4$; R being a linear or branched aliphatic hydrocarbon radical having from 1 to 24 carbon atoms, and present in the reaction mixture in an amount comprised between 0.01% and 5% by weight.

Such polymers are commercially available, for example those sold under the trademark PEMAX®, available from Elf Atochem, France, and are described, for example, in U.S. Pat. Nos. 4,331,786 and 4,332,920.

The expression undecylenic acid derivatives should be taken to mean both water-soluble as well as lipid-soluble derivatives. Such preferred derivatives are $C_1$ to $C_6$ alkyl ester derivatives, advantageously $C_1$ to $C_3$ derivatives such as the methyl, ethyl, isopropyl esters.

The composition preferably contains 50 to 10% of sequenced polyetheresteramide polymer and 50 to 90% of undecylenic acid or derivatives thereof. This gives an idea of the remarkable ability of PEEA to absorb undecylenic acid derivatives.

The composition can be used as such, in other words shaped into various functional or decorative shapes. It can be readily shaped by extrusion or molding using conventional techniques for the transformation of thermoplastic polymer materials. The composition may also contain other additives, including solvents for the acid, the said additives being present in varying amounts, generally up to 50% by weight of the final composition thus obtained.

The composition according to the invention may moreover be employed for the preparation of concentrates which, typically in granular or extrudate form, will be incorporated into other thermoplastic polymers using the master batch method. This master batch method is described, for example, in Rubber & Plastics 423283 (1961). Such thermoplastic polymers may typically be (co)polyolefins, EVA, PVC and others.

Thus in one embodiment, the present invention provides shaped articles obtained starting from the present composition.

One particular application of the present invention is the manufacture of inner soles for footwear incorporating a composition according to the invention. Such a sole can be permanently fixed within the shoe or releasable and designed for insertion within the shoe.

According to a further embodiment, the present invention provides a master batch obtained starting from the present composition.

Any technique for obtaining impregnation of the PEEA is suitable. However, it is been found that one particular process is particularly advantageous. Thus, the present invention also provides a process for preparing the composition.

According to the present invention, this process consists of incorporating undecylenic acid and/or derivatives thereof in an alcohol in a volume ratio, calculated on the basis of the acid form, comprised between 1/9 and 9/1, and then impregnating the polyetheresteramide with the mixture. The product thus obtained falls within the scope of the instant invention.

The alcohol may subsequently be partially or totally removed, e.g. by evaporation, leading thus to the final product.

The alcohol employed is preferably a $C_1$ to $C_6$ saturated alcohol, advantageously methanol.

The proportions of acid and alcohol can vary over a wide range, nevertheless, a volume ratio comprised between 1/2 and 2/1 is preferred.

DETAILED DESCRIPTION OF TYPICAL EXAMPLES

The present invention will now be exemplified by the following examples. It should be noted that throughout this specification and claims, percentages by weight are calculated on the basis of the final composition, and on the basis of the acid form as regards derivatives, except where otherwise stated.

Preparation of the composition

Two PEEAs were employed, having the commercial names PEBAX® 3533 and 2533 respectively (Elf Atochem), in the form of about 3 mm diameter spheres.

Characterization of the samples

The samples of PEBAX were characterized and the results are summarized in the table below.

| Characteristic | 3533 | 2533 |
|---|---|---|
| Weight loss over 96 hours at 40° C. | 0.22% | 0.24% |
| Fluidization point | 170° C. | |
| Solidification point | 120–130° C. | |
| Bulk density | 0.588 | 0.564 |
| 24h weight variation at 105° C.: | | |
| weight increase | 1.12% | 1.41% |

Measurement of liquid-absorption capacity

The following liquids were studied:

deionized water, ethanol, methanol, pure methyl undecylenate,

50% mixture by volume of methyl undecylenate and methanol,

50% mixture by volume of undecylenic acid and methanol.

Absorption capacity was determined in the following manner:

20 g of PEBAX spheres were immersed in 300 ml of liquid; in the case of the last mixture in the list (methanol+undecylenic acid) this was made up to 450 ml. For water, 100 g of spheres were used.

The absorption capacity was measured 24 h later at laboratory temperature. The spheres were filtered and then dried and drained on filter paper until small spheres that appeared to be dry and able to run without sticking to a glass surface were obtained. The weight and bulk volume of the swollen spheres were measured.

The results are compiled in the table below:

| Liquid absorbed | 3533 | | 2533 | |
|---|---|---|---|---|
| | weight | volume | weight | volume |
| Water (Po = 100 g) | 102.29 | 170 | 103.09 | 173 |
| Methanol (Po = 20 g) | 30.12 | 55 | 32.23 | 59 |
| (part is soluble in methanol: | 0.62 | | 0.51) | |
| Pure methyl undecylenate | 33.25 | 57 | 37.98 | 64 |
| 50% methyl undecylenate/ 50% methanol mixture | 78.69 | 140 | 152.50 | 254 |
| 50% undecylenic acid/ 50% methanol mixture | 137.77 | 220 | 251 | 360 |

The results are presented in the form of meaningful ratios, in other words by defining:

an absorption rate in weight % (T=100×(Pf-Po)/Po), a bulk density of the final spheres (d=Pf/Vf).

where

Pf is the final weight

Po is the initial weight

Vf is the final volume.

Absorption rates and density of the spheres are given in the table below.

| Liquid absorbed | 3533 | | 2533 | |
|---|---|---|---|---|
| | absorption rate % | density g/l. | absorption rate % | density g/l. |
| Water (Po = 100 g) | 2.29 | 0.302 | 3.09 | 0.596 |
| Methanol (Po = 20 g) | 50.60 | 0.547 | 61.15 | 0.546 |
| Pure methyl undecylenate | 66.25 | 0.583 | 89.90 | 0.593 |
| 50% methyl undecylenate/50% methanol mixture | 293.45 | 0.562 | 662.50 | 0.600 |
| 50% undecylenic acid/ 50% methanol mixture | 588.85 | 0.626 | 1155.00 | 0.697 |

The spheres that had absorbed methanol and methyl undecylenate maintained a certain degree of rigidity. Regarding the mixtures of methanol and undecylenic acid, the spheres adopted the appearance of a consistent gel. The methanol had a tendency to evaporate from the spheres left exposed to the air.

The presence of the absorbed products had an effect on the melting of the spheres. Sample 3533 impregnated with methyl undecylenate became fluid at 130°–140° C. and became solidified at 80° C. A weight loss of 5.73% was noted.

The same sample impregnated with undecylenic acid and methanol behaved in the following manner. Complete fluidization was observed as soon as 45°–50° C. was reached, the liquid becoming homogeneous and barely viscous at all, the evaporation point of the methanol being reached at 65° C. The liquid still remained fluid right up until complete disappearance of the methanol after which solidification occurred but, if heating was continued, the liquid remained fluid and solidification upon cooling occurred around 70° C.

A weight loss of 44.30%, in other words the part corresponding to the methanol, was observed.

The composition of the saturated spheres was as follows:

| PEBAX: | 7.96% |
|---|---|
| undecylenic acid: | 47.80% |
| Methanol: | 44.17% |

The composition of the solidified mixture was as follows:

| PEBAX: | 14.30% |
|---|---|
| undecylenic acid: | 85.72% |

The sample obtained possessed a certain degree of mechanical strength and good consistency.

Measurement of deodorizing performance of PEBAX carriers incorporating undecylenic acid and derivatives Method The approach consisted in measuring the perception threshold for the various odors tested. The experimental setup allowed two situational configurations to be tested:

dynamic phase

This approach simulated non-recycling air conditioning.

In this setup, the basic odors (unpleasant smells) were generated by a separate device (forced passage through a column) and a calibrated flow of the basic odor (q) was delivered into a further column filled with Pebax carrier modules incorporating undecylenic acid, the said flow being subsequently diluted by a flow (Q) of pure air.

The laboratory setup made it possible, using an appropriate set of valves and branch connections, to vary the ratio of basic odor to pure air flow rate (q/Q) in order to define perception thresholds for:

the basic odor (level N maximum)

the odor of the Pebax (level zero or N minimum), the odor of the basic flow passed over the Pebax (level N comprised between the two above levels).

The value for N compared to N maximum and N minimum enabled the effectiveness of the Pebax carrier incorporating undecylenic acid to be determined for the intended use.

static phase

This approach simulated an equilibrium state in a closed enclosure.

Here, the basic odors (unpleasant smells) were generated within an enclosure containing undecylenic acid incorporated in the Pebax carrier. A flow of pure air was admitted into the enclosure and collected, the contaminated and/or deodorized exiting flow (q) being mixed with a measured flow of pure air (Q), making it possible, by varying the ratio (q/Q) to define perception thresholds for:

the basic odor (level N maximum)

the odor of the Pebax (level zero or N minimum), the odor of the mixture inside the enclosure (level N comprised between the two levels above).

The value for N compared to N maximum and N minimum enabled the effectiveness of the Pebax carrier incorporating undecylenic acid to be determined for the intended use.

Results

Strong similarity was observed between the results obtained using the experimental setups designed to test the product under dynamic and static conditions.

Firstly, it could be considered that Pebax did not have any specific odor (or at least, its odor was not perceptible).

In the dynamic phase, and regardless of the rate of dilution of the polluted atmosphere, it was found that there was complete masking/deodorizing by undecylenic acid, of the following odors:

cooking smells (vapors etc. from frying)

tobacco smells.

The same applied to the tests in the static phase, using 50 g modules of Pebax carrier incorporating 20% of undecylenic acid, in 6 liter enclosures.

When a 50 g cylinder of Pebax (incorporating about 20% of undecylenic acid) was placed in a room having a volume of about 300 m³, removal of odors from this volume was noted, together with partial masking of the odors to the advantage of the odor of undecylenic acid.

What is claimed is:

1. A stable composition comprising, by weight, based on the weight of said composition:

(a) 50 to 10% by weight of a sequenced polyetheresteramide polymer of formula:

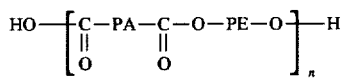

in which PA represents the polyamide segment and PE represents the polyether segment, n is an integer representing the distribution of the recurrent units; and (b) 50 to 90% by weight of a compound selected from the group consisting of undecylenic acid, alkyl ester derivatives of undecylenic acid, and mixtures thereof, the weight of said derivatives being calculated based on the corresponding weight of undecylenic acid.

2. The composition according to claim 1, in which the undecylenic acid derivative is a $C_1$ to $C_6$ alkyl ester of undecylenic acid.

3. A shaped article comprising the composition according to claim 1.

4. An inner sole for an item of footwear, said sole incorporating a composition according to claim 1.

5. A masterbatch comprising the composition according to claim 1.

6. A process for preparing a composition according to claim 1, comprising incorporating undecylenic acid and/or alkyl ester derivatives of undecylenic acid in alcohol in a volume ratio, calculated on the basis of the acid form, comprised between 1/9 and 9/1, and impregnating the polyetheresteramide with the mixture obtained.

7. The process according to claim 6 wherein the alcohol is subsequently partially or totally removed.

8. The process according to claim 6, wherein said alcohol is methanol.

9. The process according to claim 6, wherein the said ratio is comprised between 1/2 and 2/1.

10. The composition of claim 2, wherein the $C_1$ to $C_6$ alkyl ester derivatives of undecylenic acid are selected from the group consisting of methyl, ethyl and isopropyl esters of undecylenic acid.

11. The masterbatch of claim 5, wherein the alkyl esters of undecylenic acid are $C_1$ to $C_6$ alkyl ester derivatives of undecylenic acid.

12. The masterbatch of claim 11, wherein the $C_1$ to $C_6$ alkyl ester derivatives of undecylenic acid are selected from the group consisting of methyl, ethyl and isopropyl esters of undecylenic acid.

13. The process of claim 6, wherein the alkyl ester derivatives of undecylenic acid are $C_1$ to $C_6$ alkyl ester derivatives of undecylenic acid.

14. The process of claim 13, wherein said $C_1$ to $C_6$ alkyl ester derivatives of undecylenic acid are selected from the group consisting of methyl, ethyl, and isopropyl esters of undecylenic acid.

* * * * *